(12) United States Patent
Pan et al.

(10) Patent No.: US 8,858,517 B2
(45) Date of Patent: Oct. 14, 2014

(54) POWER SAVING CONTROL SYSTEM FOR NEGATIVE PRESSURE WOUND THERAPY PUMPS

(75) Inventors: Li Pan, Arcadia, CA (US); Jiang Li, Kunshan (CN); Huiyong Lin, Kunshan (CN)

(73) Assignee: Oakwell Distribution, Inc., King of Prussia, PA (US)

( * ) Notice: Subject to any disclaimer, the term of this patent is extended or adjusted under 35 U.S.C. 154(b) by 12 days.

(21) Appl. No.: 13/584,429

(22) Filed: Aug. 13, 2012

(65) Prior Publication Data

US 2013/0267917 A1 Oct. 10, 2013

Related U.S. Application Data

(60) Provisional application No. 61/620,608, filed on Apr. 5, 2012.

(51) Int. Cl.
*A61M 1/00* (2006.01)

(52) U.S. Cl.
USPC ............ 604/318; 604/317; 604/319; 604/320

(58) Field of Classification Search
CPC ............ A61M 1/0088; A61M 1/0037; A61M 1/0031; A61M 2205/18; A61M 2205/8212; A61M 2205/50; A61M 2205/8206; A61M 2205/215
USPC ......................................... 604/317–327, 543
See application file for complete search history.

(56) References Cited

U.S. PATENT DOCUMENTS

| 6,142,982 | A | 11/2000 | Hunt et al. |
|---|---|---|---|
| 7,004,915 | B2 | 2/2006 | Boynton et al. |
| 7,611,500 | B1 * | 11/2009 | Lina et al. ..................... 604/305 |
| 7,927,319 | B2 | 4/2011 | Lawhorn |
| 2005/0066961 | A1 | 3/2005 | Rand |
| 2010/0130809 | A1 | 5/2010 | Morello |
| 2010/0305523 | A1 | 12/2010 | Vess |
| 2011/0178451 | A1 * | 7/2011 | Robinson et al. ............... 602/46 |
| 2011/0264061 | A1 * | 10/2011 | Solomon et al. .............. 604/318 |
| 2012/0165764 | A1 | 6/2012 | Nicolini et al. |
| 2012/0259299 | A1 | 10/2012 | Ryu et al. |

FOREIGN PATENT DOCUMENTS

WO 2012038727 3/2012

* cited by examiner

*Primary Examiner* — Philip R Wiest
*Assistant Examiner* — Ariana Zimbouski
(74) *Attorney, Agent, or Firm* — Miller Law Group, PLLC

(57) ABSTRACT

An operating system for a medical device pump has a microprocessor controlling the operation of the pump features in a manner to minimize power consumption and maximize the life of the batteries powering the pump. The microprocessor associated with the medical device pump includes a modulation circuit that operates the pump on an intermittent basis and only when a pressure sensor indicates that the pressure asserted by the pump is at a threshold level. The operation of other sensors are powered only in situations when information from the sensor is needed, while other more essential sensors are operated on an intermittent basis by the modulation circuit. A fill sensor is operated intermittently, while a tilt sensor is only activated when a signal is received from the fill sensor. An optical sensor is only activated when the canister is removed from the pump housing, during which the pump is de-powered.

11 Claims, 5 Drawing Sheets

Fig. 3
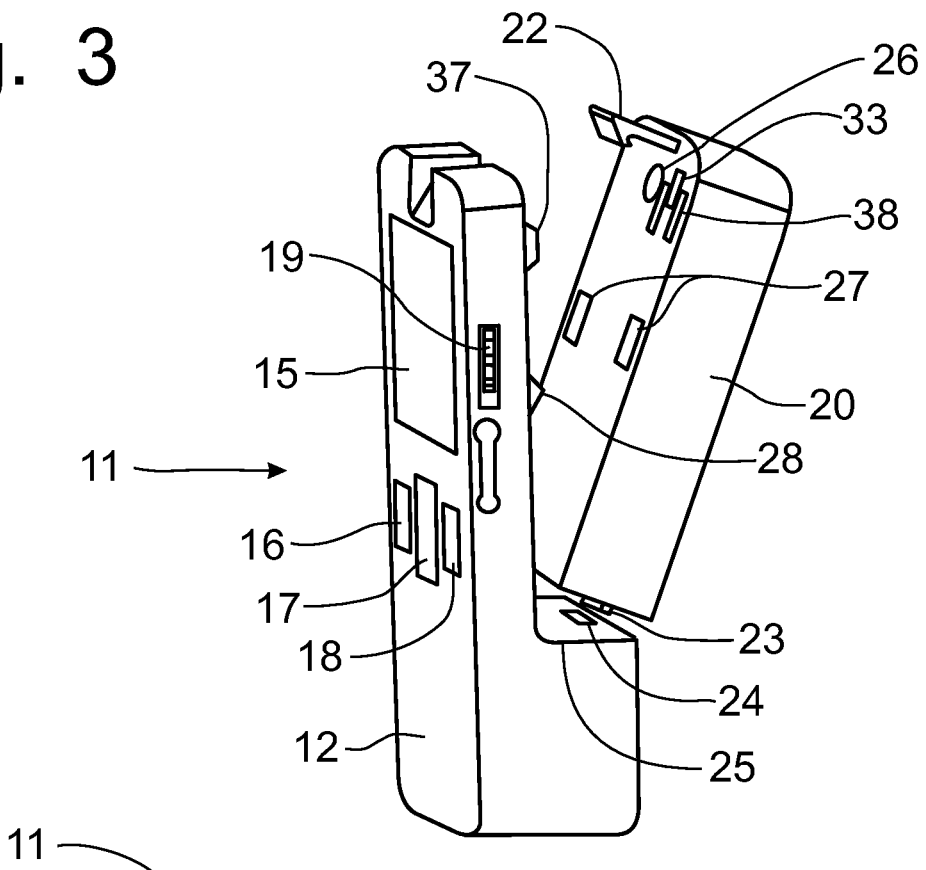
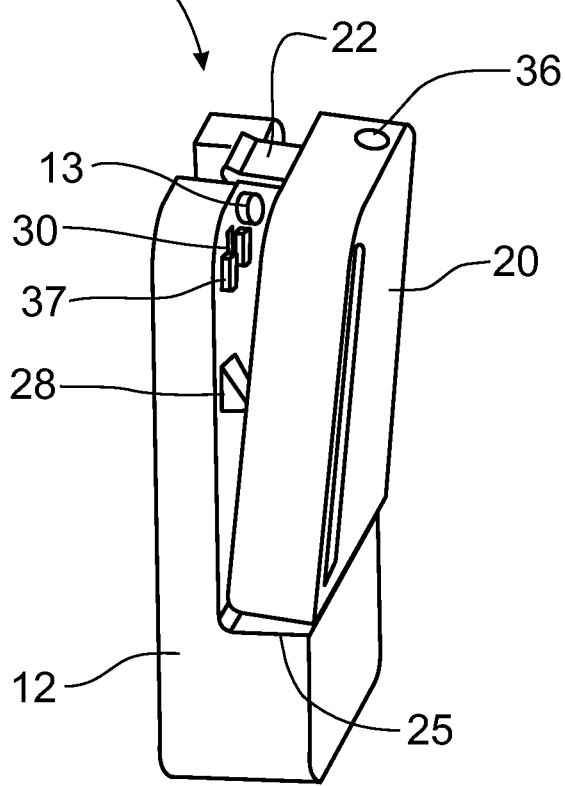
Fig. 4

POWER SAVING CONTROL SYSTEM FOR NEGATIVE PRESSURE WOUND THERAPY PUMPS

CROSS-REFERENCE TO RELATED APPLICATIONS

This application claims domestic priority on U.S. Provisional Patent Application Ser. No. 61/620,608, filed on Apr. 5, 2012, the content of which is incorporated herein by reference.

FIELD OF THE INVENTION

The present invention relates generally to negative pressure wound therapy system and, more particularly, to a control system that will control energy consumption from the battery powering the operation of the negative pressure pump.

BACKGROUND OF THE INVENTION

Negative pressure wound therapy involves a bandage system that is applied to the wound site on the patient to create a seal around the perimeter of the bandage system and around a periphery of the wound to be treated. The negative pressure bandage system is provided with a connector that connects to a pump that draws a vacuum on the bandage system to urge any fluid and exudates within the wound site to move toward the pump through a conduit interconnecting the connector and the pump. A canister is connected to the conduit to intercept the fluids and exudates before reaching the pump to collect the fluids and exudates until the canister is filled to a predetermined level. Preferably, the canister can be removed from the pump housing and replaced when filled.

In U.S. Pat. No. 6,139,982, granted to Kenneth W. Hunt, et al on Nov. 7, 2000, a negative pressure wound therapy apparatus is disclosed in which a canister is removably mounted in a pump housing and connected by a conduit to the pump to draw a vacuum on the canister. A separate conduit connects the canister to the negative pressure bandage system to draw the fluids and exudates from the wound being treated into the canister. A filter is provided at the outlet end of the canister where the conduit interconnecting the canister and the pump is located to prevent the introduction of the fluids and exudates collected into the canister from the bandage system into the pump.

U.S. Pat. No. 7,004,915, issued to Thomas A. Boynton, et al on Feb. 28, 2006, discloses a canister that is connected by a first conduit to the negative pressure bandage system and by a second conduit to the pump that asserts a negative pressure on the canister through the second conduit, which vacuum is asserted through the canister to the first conduit and the connected bandage system. The canister incorporates first and second hydrophobic filters at the connection of the second conduit to the canister such that the first hydrophobic is adapted to operate as a fill sensor for the canister and the second hydrophobic filter further inhibits contamination of the pump by the collected fluids and exudates from the wound site. An odor filter is also provided between the first and second hydrophobic filters to counteract the production of malodorous vapors present in the collected wound exudates.

In U.S. Pat. No. 7,611,500, granted on Nov. 3, 2009, to Cesar Z. Lina, et al, the canister includes an outlet that is plugged onto a port supported on the pump housing to connect the canister with the vacuum source. A switch carried on the pump housing closes when the canister is properly seated on the port. The canister incorporates a filter cap that allows the pump to draw air from the canister through the port and assert a vacuum on the negative pressure bandage system. The canister also incorporates a fill sensor in the form of a capacitive sensor that identifies a change in capacitance within the canister corresponding to the fluid level reaching the fill sensor located on the side of the canister near the outlet.

U.S. Pat. No. 7,927,319, granted on Apr. 19, 2011, to Thomas Lawhorn, et al, discloses a leak detection system in a negative pressure wound therapy apparatus by monitoring the power consumption of the pump in comparison with a target power level such that a processing unit comparing the actual power level of the pump to a target power level triggers an alarm when the actual power level is greater than the target power level for a predetermined period of time, which identifies the presence of a leak in the exudates collection apparatus. In U.S. Pat. No. 7,876,546, granted to Christopher Locke, et al, on Jan. 25, 2011, discloses a modular component system for a negative pressure wound therapy apparatus that is respectively operated by the software driven control system.

In each of the above-described negative pressure wound therapy devices, the fluids and exudates are drawn from the negative pressure bandage directly into the canister where the fluids and exudates are collected. Typically, the movement of the fluids and exudates is restricted from contaminating the pump by a hydrophobic filter that prevents the fluids and exudates from entering the vacuum line to the pump. The canister is preferably removable from the pump housing and disposed when filled, to be replaced by a new canister. With fill sensors specifically located on the canister, orientation of the canister is highly critical to prevent the fluids from being sensed by the fill sensor.

Many known negative pressure wound therapy systems commercially available are portable devices, meaning that the pump and the canister are sufficiently small as to be capable of being attached to the patient and moved from one location to another as the patient moves about. The power to operate the pump is provided by a battery or by a battery pack that enables the negative pressure wound therapy apparatus to be completely portable. Powering a multi-component apparatus from disposable batteries having limited stored energy is difficult to maintain. Replacement of the bandage is typically performed by a medical care professional, at which time the disposable batteries can be easily replaced without interrupting the operation of the negative wound therapy. With a target of bandage replacement every 48-72 hours, battery power should preferably last for at least 72 hours before requiring replacement.

It would thus be desirable to provide a control system for a multi-component negative pressure wound therapy apparatus that would provide energy saving function to enable the disposable batteries to operate the pump continuously for at least 72 hours. It would also be desirable to provide a software driven control system for a negative pressure wound therapy apparatus that is operable to conserve energy consumption.

SUMMARY OF THE INVENTION

It is an object of this invention to overcome the disadvantages of the prior art by providing an energy saving operating system for a battery operated pump.

It is another object of this invention to provide an energy saving operating system for the pump utilized in a negative pressure wound therapy system.

It is an advantage of this invention that the battery powered pump will be operable for a maximum length of time without requiring a change of batteries.

It is a feature of this invention that all non-essential features of the pump are shut down by the operating system until an operation of the feature is required.

It is another feature of this invention that the fill sensor for the pump is operated intermittently to check levels within the canister collecting fluids from a negative pressure bandage.

It is still another feature of this invention that the tilt sensor is actuated only if a signal is received from the fill sensor.

It is yet another feature of this invention that the display screen is deactivated until a message needs to be sent from the microprocessor to the user of the negative pressure wound treatment apparatus.

It is another advantage of this invention that the pump is operated intermittently and only when a pressure sensor provides an indication that the negative pressure is at a threshold value.

It is a further feature of this invention that the optical sensor used to determine if the canister is properly mounted on the pump housing is activated only when the canister is removed from the pump housing until the canister has been properly mounted.

It is still a further feature of this invention that the pump is not operated when the optical sensor is activated.

It is yet another advantage of this invention that the power consumption of the pump is minimized while providing an effective operation of the pump.

It is still another object of this invention that the pump includes a microprocessor to control the operation of the pump with the microprocessor incorporating a modulation circuit.

It is a further advantage of this invention that the modulation circuit provides an intermittent operation of the pump as required by the microprocessor for the operation of the medical device associated with the pump.

It is yet another object of this invention to provide a medical device pump with an operating system which is durable in construction, carefree of maintenance, and simple and effective in use.

These and other objects, features and advantages are accomplished according to the instant invention by providing an operating system for a medical device pump in which the microprocessor controls the operation of the pump features in a manner to minimize power consumption and maximize the life of the batteries powering the operation of the pump. The microprocessor associated with the medical device pump includes a modulation circuit that operates the pump on an intermittent basis and only when a pressure sensor indicates that the pressure asserted by the pump is at a threshold level. The operation of other sensors are powered only in situations when information from the sensor is needed, while other more essential sensors are operated on an intermittent basis by the modulation circuit. A fill sensor is operated intermittently, while a tilt sensor is only activated when a signal is received from the fill sensor. An optical sensor is only activated when the canister is removed from the pump housing, while the pump is de-powered whenever the optical sensor is activated.

BRIEF DESCRIPTION OF THE DRAWINGS

The foregoing and other objects, features, and advantages of the invention will appear more fully hereinafter from a consideration of the detailed description that follows, in conjunction with the accompanying sheets of drawings. It is to be expressly understood, however, that the drawings are for illustrative purposes and are not to be construed as defining the limits of the invention.

FIG. 3 is a left side perspective view of the pump and canister shown in FIGS. 1 and 2, but depicting the initial engagement of the canister onto the pump housing;

FIG. 4 is a left side perspective view of the pump and canister shown in FIG. 3, but having the canister about to latch onto the pump housing;

DETAILED DESCRIPTION OF THE PREFERRED EMBODIMENT

Figure 1:
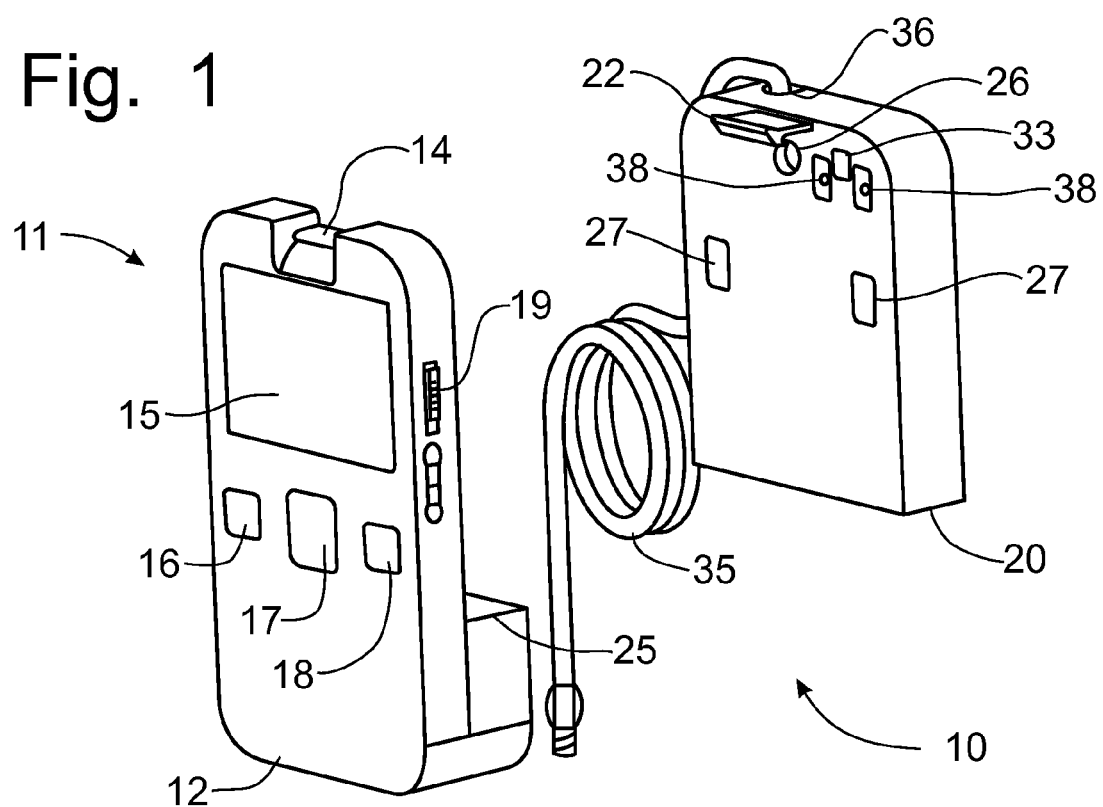
FIG. 1 is an exploded front perspective view of a negative pressure wound system pump and canister incorporating the principles of the instant invention.
Figure 2:
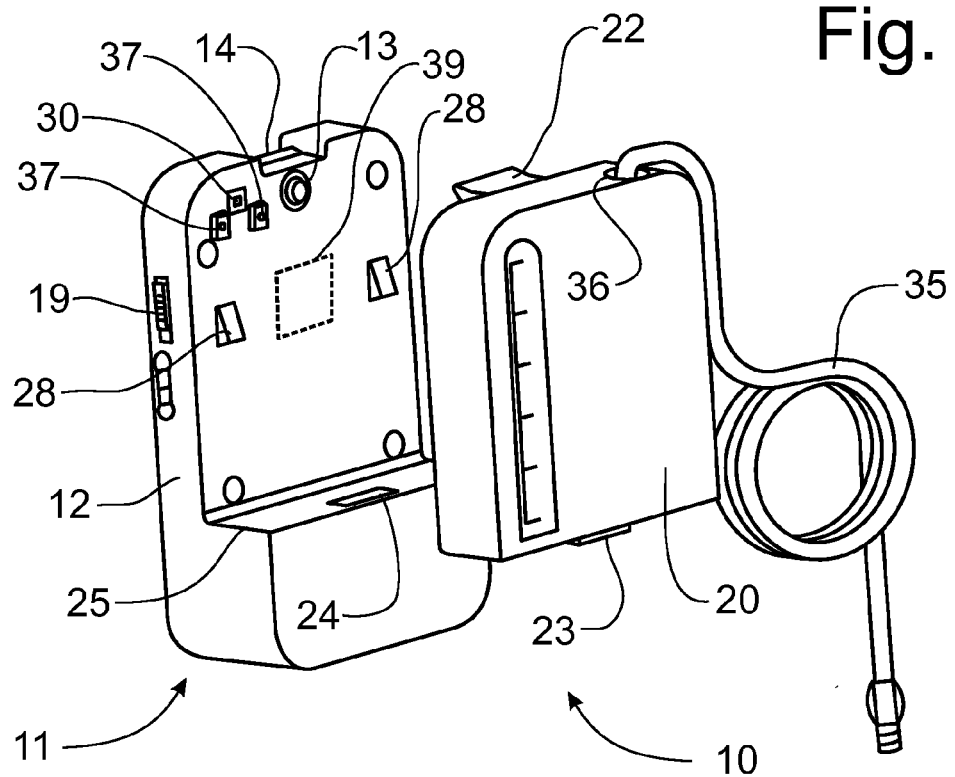
FIG. 2 is an exploded rear perspective view of the negative pressure wound system pump and canister shown in FIG. 1.

Referring to FIGS. 1-5, a pump for a negative pressure wound therapy system 10 can best be seen. The system 10 includes a pump 11 mounted in a pump housing 12 that draws a vacuum from the vacuum port 13 for the purposes of extracting fluids and exudates from a negative pressure bandage 34, as will be discussed in greater detail below. The pump housing 12 is provided with a display screen 15 and control buttons 16-19 for operating of the pump 11 and monitoring the function thereof. The top surface of the pump housing 12 is formed with a latch keeper 14 to retain the canister 20 on the pump housing in operative communication therewith, as will also be described in greater detail below. In the way of examples, the control buttons 16-19 can provide operations control for the pump 10. The control button 16 can be used to set the operating pressure for the pump 10. Control button 17 can be used to turn the pump 10 on and off to start or stop the negative pressure therapy. Control button 18 can define the mode of operation, such as continuous or intermittent operation of the pump 10. Control switch 19 can be used to turn the electronics on and off, the powering of the electronics being necessary before the other control buttons 16-18 can be operated.

The canister 20 is a hollow structure for collecting and storing the fluids and exudates extracted from the negative wound therapy bandage 34. The canister 20 is detachably supported on the mounting ledge 25 of the pump housing 12 and operatively cooperable therewith to receive a vacuum therefrom and to apply that vacuum to the negative pressure bandage 34 to extract fluids and exudates therefrom. The canister 20 is formed with a latch member 22 at the upper edge thereof to be positionable for engagement with the latch keeper 14 on the pump housing 12. Also, the bottom surface of the canister 20 is formed with a mounting tab 23 that is sized to insert into a positioning slot 24 formed in the housing ledge 25 to secure the canister 20 on the pump housing 12 and to assure that the canister 20 is properly mounted on the pump housing 12.

The canister 20 is provided with a receiver port 26 that is aligned with the vacuum port 13 when the canister 20 is properly mounted on the pump housing 12 so that the pump 11 can draw a vacuum on the canister 20. The canister 20 is also provided with retainer holes 27 that receive retainer tabs 28 formed on the pump housing 12 to stabilize the positioning of the canister 20 on the pump housing 12. The process to mount the canister 20 on the pump housing 12 is shown in FIGS. 3 and 4. The canister 20 is first positioned on the ledge 25 of the pump housing 12 so that the mounting tab 23 slides into the corresponding positioning slot 24. The canister 20 is then rotated about the mounting tab 23 until the latch 22 snaps over the latch keeper 14 to secure the canister 20 onto the pump housing 12. If the canister 20 is properly aligned, the retainer tabs 28 will fit into the corresponding retainer holes 27 to provide lateral stability for the canister 20 relative to the pump housing 12.

Because of the required connection of the vacuum port 13 within the receiver port 26 to enable proper operation of the negative pressure wound therapy system 10, the pump housing 12 is provided with an optical sensor 30 that directs an infrared light onto a reflector 33 mounted on the canister 20. If the reflector 33 is not properly aligned, i.e. perpendicular to the optical sensor 30, the infrared light beam will not be reflected back into the infrared optical sensor 30. The pump 11 is operably connected to the optical sensor 30 such that the receipt of a return signal from the reflector 33 is required in order for the pump 11 to be activated. Preferably, the optical sensor 30 will initiate a message on the display screen 15 to alert the user that the canister 20 is or is not properly aligned for operation of the pump 11.

Figure 5:
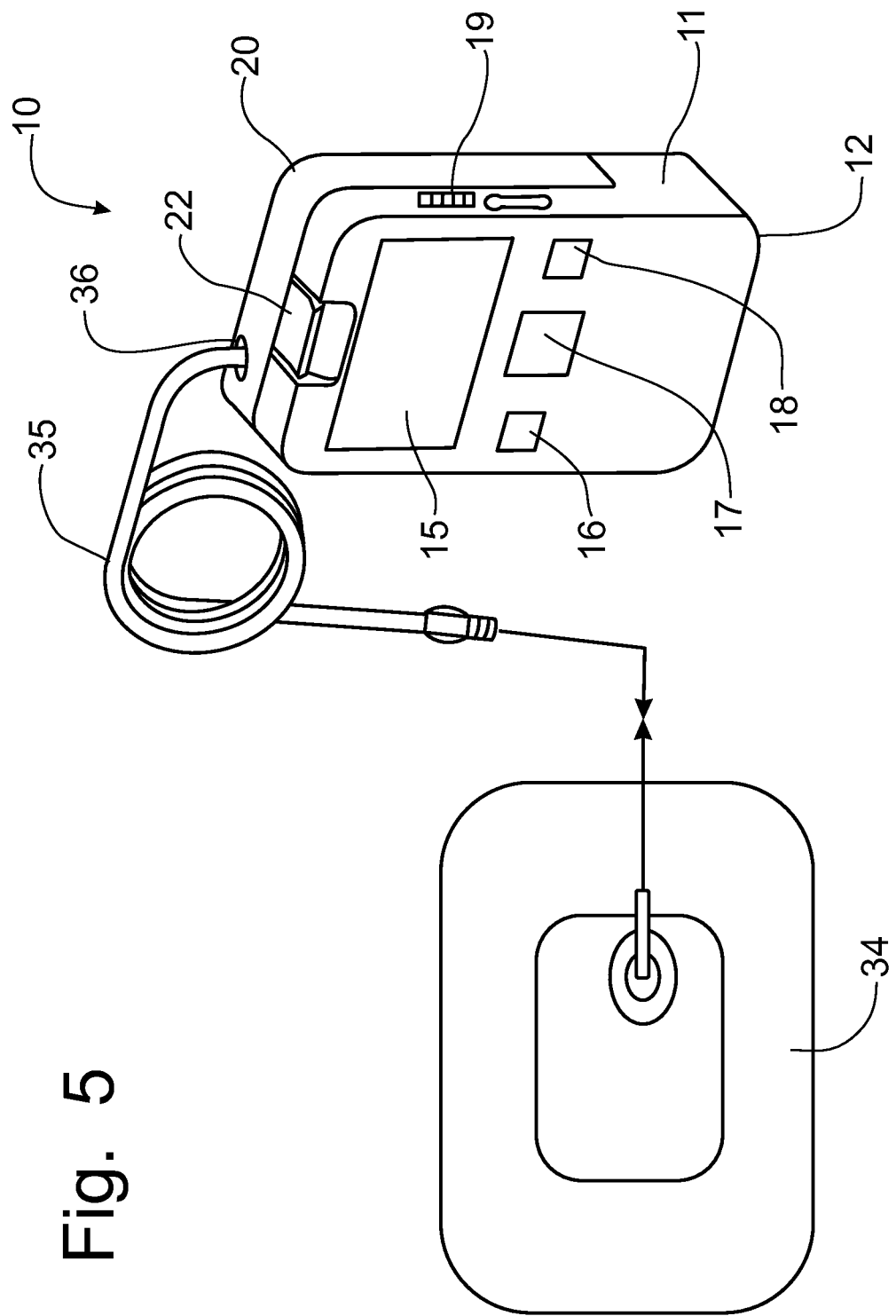
FIG. 5 is a front perspective view of a negative pressure wound system with the assembled pump and canister connected to a negative pressure bandage.

Once the canister 20 is properly seated on the pump housing 12, the pump 11 is free to operate and draw a vacuum through the vacuum port 13 engaged with the receiver port 26 into the canister 20, which is turn is applied to the tubing 35 connected to the inlet port 36 of the canister 20 and extending to the negative pressure bandage 34, as is shown in FIG. 5. Fluids and exudates are drawn into the canister 20 via the tubing 35 and fall to the bottom of the canister 20. A hydrophobic filter (not shown) is preferably utilized on the interior side of the receiver port 26 to prevent the fluids and exudates from entering into the pump 11 via the vacuum port 13.

Figure 7:
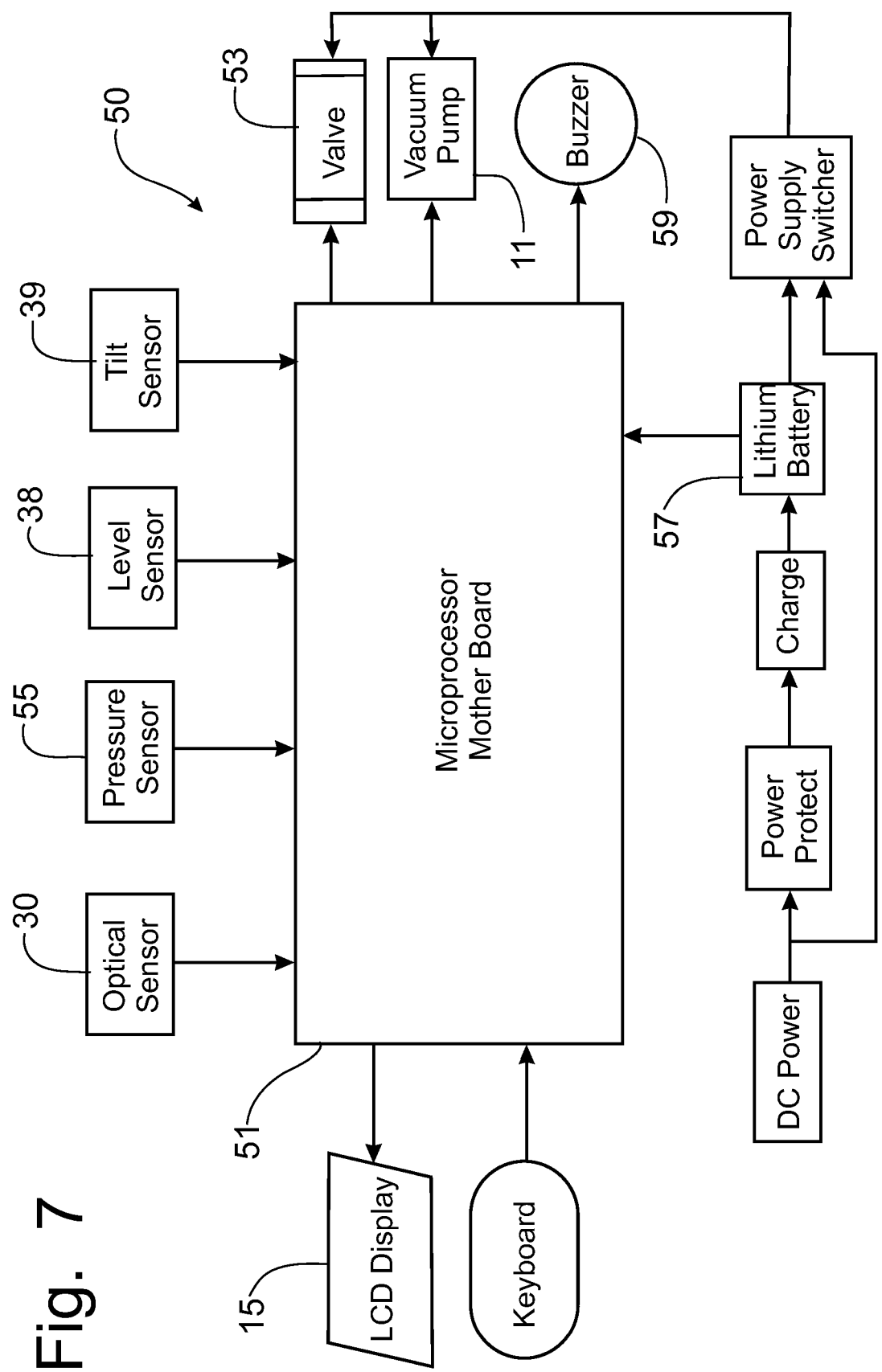
FIG. 7 is a schematic block diagram representing the control logic functions.

The canister 20 is provided with a pair of resister-type fill sensors 38 that project into the interior of the canister 20 and are connected to the microprocessor 51 mounted in the pump housing 12 via the contacts 37, as is depicted in the schematic block diagram of FIG. 7. The fill sensors 38 are positioned adjacent the optical sensor 30 and the reflector 33 and provide a signal to the microprocessor 51 that fluid is cross-connecting the two fill sensors 38 which allows electrical current to cross from one fill sensor 38 to the other. The completion of that electrical circuit signals the microprocessor 51 that the fill sensors 38 are being engaged by fluid within the canister 20. In addition, the pump housing 12 supports a tilt sensor 39 that can determine the direction and the angle at which the pump housing 12, and therefore the canister 20, is oriented. The signals from both the tilt sensor 39 and the fill sensors 38 are sent to the microprocessor 51 to control the operative function of the pump 11.

Figure 6:
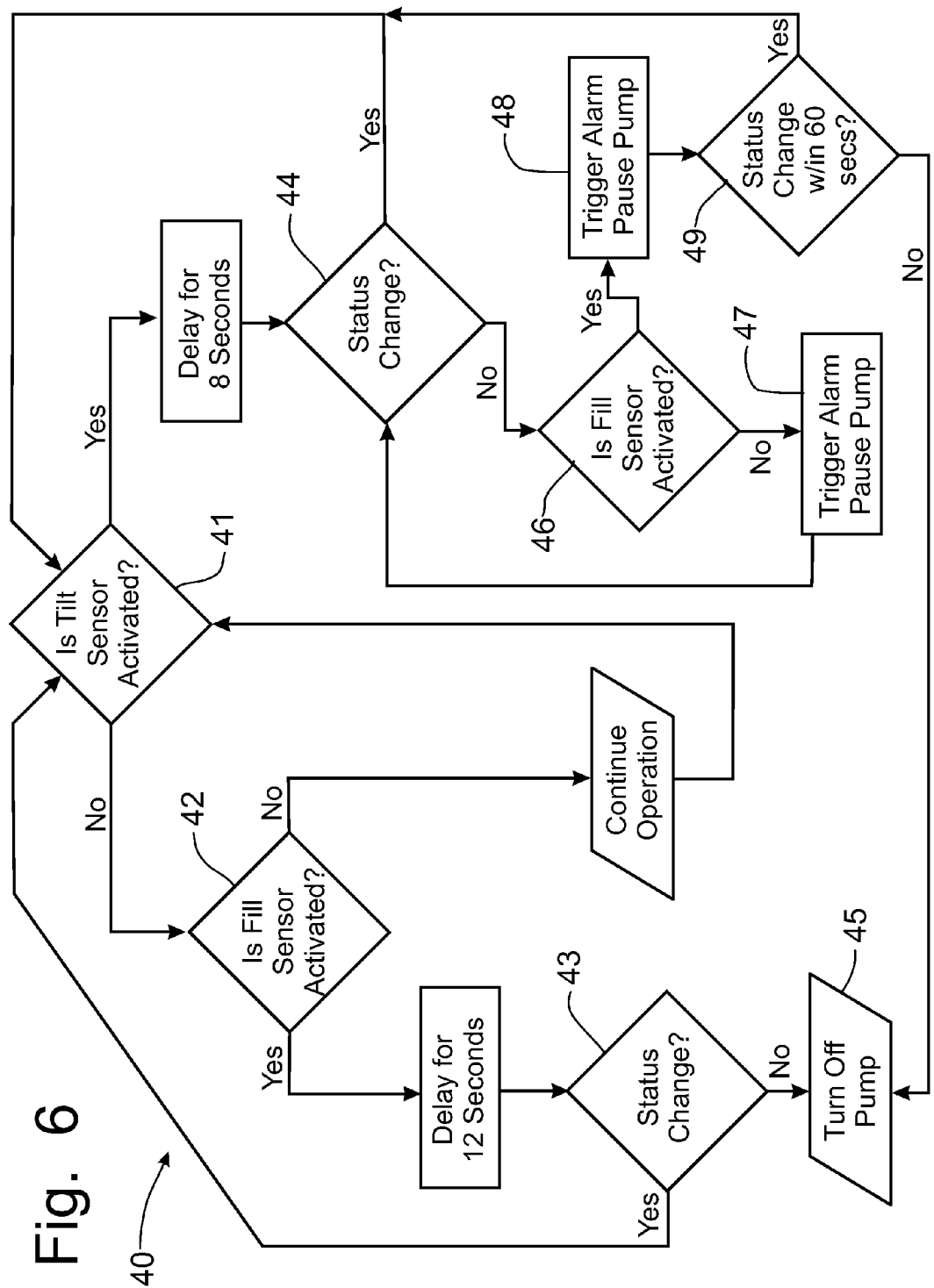
FIG. 6 is a logic flow diagram reflecting the operation of the tilt and level sensors in the control of the pump.

As can be seen in FIG. 6, the combination of the signals from the fill and tilt sensors 38, 39, will control the operation of the pump 11. The negative pressure therapy system 10, specifically the pump 11 and canister 20, will work most efficiently when the canister is oriented in an upright position. Thus, when the canister 20 is not in the upright position, the user needs to be informed of the inappropriate orientation so that the user can correct the orientation of the canister 20. Preferably, the tilt sensor 39 will be able to ascertain the number of degrees of the tilt, but will have some latitude with respect to accuracy. For example, identifying the canister 20 at a vertical orientation can encompass a vertical orientation plus or minus a few degrees.

As shown in FIG. 6, the process 40 begins at step 41 with a query as to whether the tilt sensor 39 is activated. If the tilt sensor 39 is not activated, the next query at step 42 defines whether the fill sensor 38 has been activated. If the fill sensor has not been activated, the operation of the pump 11 would continue as intended. If the fill sensor 38 has been activated at step 42, the process is delayed for about twelve seconds and then at step 43 to provide assurance that the fill sensors 38 are not being activated by a splashing of the fluids within the canister 20, which would present a false alarm. After the delay circuit is exhausted, the process 40 queries at step 43 whether either the fill sensor 38 or tilt sensor 39 status has changed. If no change in status is ascertained at step 43, then the pump 11 is turned off automatically at step 45 as the canister 20 is full. If the status at step 43 has changed, the process starts again at step 41.

If at step 41, the tilt sensor 39 has been activated, the process delays activity for eight seconds to provide a safeguard against a false signal due to movement of the canister 20 splashing fluids onto the fill sensors 38. Then at step 44, the process queries whether the tilt sensor 38 has undergone a status change. If at step 44 the tilt sensor 39 has a changed status, the process returns to step 41 to query if the tilt sensor 39 has been activated. If the response to the query at step 44 is in the negative, the process 40 queries the fill sensor 38 at step 46 to see if the fill sensor 38 has been activated. If the fill sensor 38 has not been activated, the process triggers an alarm, preferably both audible and visual, at step 47, to inform the user to reorient the canister 20, while the operation of the pump is paused until the canister has been returned to a vertical orientation.

The process 40 then returns to step 44 to see if the status of the tilt sensor 39 has changed. The alarm will not be disengaged nor the pump returned to operation until the status of the tilt sensor 39 has changed at step 44. If at step 46 the fill sensor 38 has been activated, the alarm is also triggered and the operation of the pump 11 is paused. If after sixty seconds at step 49 the status of the fill sensor has changed, then the process returns to step 41 to determine if the tilt sensor 38 is still activated. If at step 49 both the fill and tilt sensors 38, 39 remain activated, then the process will automatically shut down the pump 11 at step 45.

Referring now to the schematic diagram of the control system 50 in FIG. 7, one skilled in the art can see that the microprocessor 51 receives input from the fill and tilt sensors 38, 39, to control the operation of the pump 11 in the manner described above. Furthermore, the optical sensor 30 is connected to the microprocessor 51 to control the initial start up of the pump 11. Without the confirmation signal from the optical sensor 30, the microprocessor 51 will not allow the pump 11 to start operation. The microprocessor 51 also receives confirmation signals from a pressure sensor 55 to monitor the negative pressure asserted through the vacuum port 13. If the pressure rises or falls significantly, the pump 11 will also cease operating and provide a message to the user by the display screen 15 to inform the user of a pressure problem, which could be caused by a failure of the pump 11, a plugged tubing 35, or an overfilled canister 20, among other things. The visual display of an alarm or of an error message or the like, is provided to the user via the LCD display screen 15 while the auditory alarm or signal is provided via a buzzer 59 operatively coupled to the microprocessor 51.

The control system 50 is operated by the software driven microprocessor 51 to control the respective components of the negative pressure wound therapy system 10 in a manner to conserve energy consumption from the disposable batteries 57. Preferably, the components requiring power to operate, including the pump 11, the valve 53, the alarm 59, and the LCD display screen 15, including the LED indicator light and the screen back light, are selected to be of a low power consumption type for use in the system 10. The pump 11 is the component that consumes the most energy to operate in drawing the fluids and exudates from the bandage 34 to the canister 20 for collection and removal from the system 10. To control the energy consumption of the pump 11, the microprocessor 51 incorporates a modulation circuit that is operable to drive the pump only when pressure in the canister 20 has dropped below a threshold level as sensed by the pressure sensor 55. Thus, the pump 11 is not operated continuously, but intermittently, to maintain an effective operating vacuum within the canister 20 and the tubing 35 to the bandage 34.

All key components in the system 10 are controlled by the software stored in the microprocessor 51 in a manner that each respective component is only turned on to operate whenever the component is needed for operation of the negative pressure wound therapy system 10. The valve 53 is operatively associated with the pump 11 to open and close when needed to allow the pump 11 to increase the level of the negative pressure applied to the canister 20 to a threshold level above the threshold level required for the activation of the pump 11 as indicated by the pressure sensor 55. Thus, the valve 53 isolates the bandage 34 from the pump 11 when closed and is opened only when needed for the pump 11 to operate as defined by the pressure sensor 55. Furthermore, not all of the sensor circuits will be active during the operation of the system 10, unless the circuit is needed for operation of the system 10. For example, the circuit for the optical sensor 30 is only active whenever the canister 20 is disengaged from the pump housing 12. The circuit for the tilt sensor 39 can be turned off until the level sensor 38 indicates that the canister 20 appears to be filled. Then, the tilt sensor 39 and the level sensor 38 can operate as reflected in FIG. 6. The LCD display 15 can be deactivated unless the microprocessor 51 determines that a message needs to be sent to the user, such as an error message, or unless the user is selecting one of the control buttons 16-18 to make system adjustments or inquiries.

A side benefit to the deactivation of components not absolutely needed for the operation of the negative pressure wound therapy system 10 is that the system 10 will have a quieter operation. With the pump 11 operating intermittently, the overall noise production of the pump 11 will be significantly lower than with a continuously operated pump 11. Furthermore, the deactivation of key components and nonessential circuits also reduces noise production. As a result, the energy saving function of the microprocessor 51 will provide a more quietly operating system 10.

The invention of this application has been described above both generically and with regard to specific embodiments. Although the invention has been set forth in what is believed to be the preferred embodiments, a wide variety of alternatives known to those of skill in the art can be selected within the generic disclosure.

Having thus described the invention, what is claimed is:

1. A method of operating a battery-powered medical device having a pump providing a vacuum to an associated negative pressure wound therapy apparatus, said medical device having a microprocessor and operative components coupled to said microprocessor to minimize power consumption from the battery, comprising the steps of:
providing said microprocessor with a modulation circuit, said modulation circuit powering the operation of said pump only when a pressure sensor associated with the vacuum applied to said negative pressure wound therapy apparatus indicates that the negative pressure of the vacuum is at a threshold level;
operating said pump and a selected first portion of said operative components intermittently through said modulation circuit as required by said microprocessor for operation of said medical device and operating a selected second portion of said operative components in response to the operation of said first portion of said operative components, one of said second portion of said operative components including a tilt sensor associated with said pump to provide a signal to said microprocessor when said pump is in a non-vertical position, one of said first portion of said operative components being a fill sensor providing a signal to said microprocessor when a canister associated with said pump is filled with fluid from the operation of said negative pressure wound therapy apparatus;
intermittently operating said fill sensor through said modulation circuit to check fluid levels within said canister; and
activating said tilt sensor only when the microprocessor receives a signal from said fill sensor indicating activation thereof by fluids within said canister.

2. The method of claim 1 further comprising the step of:
deactivating a display screen associated with said pump until the microprocessor determines that a message needs to be sent to the user of the negative pressure wound therapy apparatus.

3. The method of claim 1 wherein the pump includes a valve isolating the vacuum applied to said negative pressure wound therapy apparatus from said pump when closed, said valve being opened by said microprocessor when said pump is operated to apply negative pressure to said negative pressure wound therapy apparatus.

4. The method of claim 1 further comprising the step of:
powering an optical sensor through said microprocessor only when said canister is disengaged from said pump, said microprocessor de-powering said pump as long as said optical sensor is powered.

5. A method of operating a battery-powered negative pressure wound therapy apparatus including a pump that provides a vacuum to a remote bandage, said pump including a housing on which is mounted a removable canister for storing fluids and exudates received from said bandage, said negative pressure wound therapy apparatus further including a microprocessor and operative components coupled to said microprocessor to minimize power consumption from the battery, comprising the steps of:
providing said microprocessor with a modulation circuit;
operating said pump through said microprocessor and only in response to a pressure sensor associated with the vacuum applied to said bandage that indicates that the negative pressure of the vacuum is at a threshold level; and
activating a tilt sensor associated with said pump by said microprocessor only in response to the microprocessor receiving a signal from a fill sensor indicating activation thereof by fluids within said canister.

6. The method of claim 5 wherein said fill sensor is activated intermittently by the modulation circuit in said microprocessor to check fluid levels within said canister.

7. The method of claim 5 wherein the microprocessor deactivates all components of the pump until needed to maintain operation of said bandage.

8. The method of claim 5 wherein the pump includes a valve located between the pump and the bandage to isolate the negative pressure within the bandage from the pump, said valve being opened by said microprocessor in response to said pump is operated.

9. The method of claim 5 further comprising the step of:
deactivating a display screen until the microprocessor determines that a message needs to be sent to the user.

10. The method of claim 5 further comprising the step of:
powering an optical sensor through said microprocessor in response to said canister being disengaged from said housing.

11. The method of claim 10 wherein said microprocessor will not conduct said step of operating said pump while said optical sensor is powered.

* * * * *